United States Patent [19]

Garcia et al.

[11] Patent Number: 4,468,951
[45] Date of Patent: Sep. 4, 1984

[54] PERMEATION TESTING APPARATUS

[76] Inventors: David B. Garcia, 11409 Taterwood Dr., Austin, Tex. 78750; Bruce A. Sorenson, 44 Springlake, Dripping Springs, Tex. 78620; Lawrence H. Keith, 7605 Rock Point Dr., Austin, Tex. 78731; James M. Harless, 10005 Blue Martin, Austin, Tex. 78750; Douglas B. Walters, 6807 Breezewood Rd., Raleigh, N.C. 27607; Andrew T. Prokopetz, B-6 Village Green, Chapel Hill, N.C. 27514

[21] Appl. No.: 459,953

[22] Filed: Jan. 21, 1983

[51] Int. Cl.³ .......................................... G01N 15/08
[52] U.S. Cl. ..................................................... 73/38
[58] Field of Search ...................................... 73/38, 37

[56] References Cited
U.S. PATENT DOCUMENTS

| | | | |
|---|---|---|---|
| 3,548,634 | 12/1970 | Roy | 73/38 |
| 3,590,634 | 7/1971 | Pasternak et al. | 73/38 |
| 3,604,246 | 9/1971 | Toren | 73/38 |

Primary Examiner—Gerald Goldberg
Assistant Examiner—Hezron E. Williams
Attorney, Agent, or Firm—Stefan J. Klauber

[57] ABSTRACT

A permeation testing apparatus for determining the permeation of a chemical through a test material. The testing apparatus includes a permeation cell comprising two units, each constructed of a block of relatively chemically inert material which may be placed in intimate contact. One face of each said block has a shallow cylindrical well, that is referred to as the "challenge side". The opposite face of the block has a conical well that is referred to as the "collection side". Two such blocks, or permeation units, are positioned face-to-face ("challenge side" to "collection side") and constitute one permeation cell. The material to be tested is positioned between two permeation units thereby separating the "challenge side" from the "collection side". Four ports are provided perpendicular to the axes of the permeation cell; i.e., an inlet and an exit port for each of the two permeation units. Several permeation units may be stacked, with each interface providing a permeation cell. The number of cells is then one less than the number of permeation units.

19 Claims, 8 Drawing Figures

PERMEATION TESTING APPARATUS

FIELD OF THE INVENTION

This invention relates generally to apparatus for determining permeation of solid, liquid or gaseous chemicals or mixtures of chemicals through a material, and more specifically relates to a device for measuring of chemical permeation through various materials, using very small amounts of the chemical and optionally using small sections of the test material.

BACKGROUND OF THE INVENTION

The American Society for Testing and Materials (ASTM) has devised a test procedure for determining the resistance of protective clothing materials to permeation by hazardous liquid chemicals, which has been published as ASTM Designation F739-81. This procedure was developed to protect workers involved in the production, use, and transportation of liquid chemicals, who are, and can be exposed to numerous compounds capable of causing harm upon contact with the human body. The deleterious effects of these chemicals can range from acute trauma, such as skin irritation and burn, to chronic degenerative disease, such as cancer. Since engineering controls may not eliminate all possible exposures, attention is often placed on reducing the potential for direct skin contact through the use of protective clothing that resists permeation, penetration, and degradation.

The resistance of a protective clothing material to permeation by a hazardous liquid chemical is determined by measuring the breakthrough time, then monitoring the subsequent permeation rate of the hazardous liquid through the clothing material.

In the ASTM permeation test cell, the clothing material acts as a barrier separating the hazardous liquid chemical from a collecting medium. The collecting medium, which can be a liquid or a gas, is sampled and analyzed quantitatively to identify the concentration of hazardous chemical in it and thereby the amount of hazardous chemical that has permeated the barrier as a function of time after initial liquid contact.

This method is normally used to evaluate flat specimens from finished items of protective clothing and from materials that are candidates for items of protective clothing. Finished items of protective clothing include gloves, arm shields, aprons, suits, hats, boots, respirators, and the like.

The phrase "specimens from finished items" encompasses seamed and other discontinuous regions as well as the usual continuous regions of protective clothing items.

By measuring breakthrough time, this method is used to estimate the duration of maximum protection provided by a protective clothing material under the condition of continuous contact. By measuring the permeation rate, this mmethod can be used to identify protective clothing materials that limit potential exposures to acceptable steady-state dermal contact levels.

The ASTM currently recommends the use of an all glass permeation cell as described in its aforementioned standard F739-81. However, this cell requires relatively large volumes (approximately 60 mL) of liquid for a single evaluation, and requires as well relatively large pieces of test material (approximately 20 cm$^2$).

In addition, the all glass construction of the ASTM cell renders it easily damaged. Moreover, when ASTM methodology is used, a total of at least 180 mL of liquid is necessary, since triplicate analyses are required. Such volumes are dangerous when working with hazardous chemicals.

Furthermore, because of the large volume of liquid required, testing of inherently expensive or scarce chemicals tend to be prohibited by the current ASTM cell.

The aforesaid ASTM standard designation F739-81 is incorporated herein by reference for the purposes of comparison.

SUMMARY OF THE INVENTION

In accordance with the present invention, a permeation cell is provided which overcomes the foregoing and other problems, by permitting tests to be conducted with as little as 1.0–2.0 cc of test chemical.

The permeation cell, according to the invention, may be constructed of any relatively chemically inert machinable or other formed material, including but not limited to, high-density plastic, Teflon ®, stainless steel, glass, and the like. The individual permeation unit is a block that is typically machined on both faces. One face has a shallow cylindrical well that is referred to as the "challenge side". The opposite face has a conical well that is referred to as the "collection side". Two such blocks, or permeation units, positioned face-to-face ("challenge side" to "collection side") constitute one permeation cell. The material to be tested is positioned between two permeation units, thereby separating the "challenge side" from the "collection side". Four ports are provided directly perpendicular to the axes of the permeation cell; i.e., an inlet and an exit port for each of the two permeation units.

Since the permeation units are machined on the two parallel faces, they provide the option of stacking numerous such units. Each interface provides a permeation cell. The number of permeation cells in such a stack is defined as "n-1 permeation units" where "n" is an integer. For example, five such permeation units in a stacked configuration positioned face-to-face ("challenge side" to "collection side") are capable of testing four membranes (i.e. test materials) and, thus, constitute four permeation cells.

To operate the permeation cells, two or more permeation units are put together, each with a piece of the material to be tested placed flat between the "challenge side" and the "collection side". Three (or more) bolts are then tightened to squeeze the test material pieces tightly between the permeation units so there will be no leaks of the test chemical around the test material. The test chemical is then introduced into the "challenge side" of the test cell using a syringe or any other convenient method of introduction. The collecting medium is then passed through the "collection side" of the permeation cells. All or any portion of the collecting medium is then subjected to an appropriate analytical technique to measure detectable concentrations of the test chemical that permeate through the test material.

Accordingly, it is an object of the invention to provide a device for testing permeation of chemicals through a material, requiring a relatively small amount of the chemical and optionally a relatively small piece of the material.

It is a further object of the invention to provide a device which will quickly and easily determine the permeation of chemicals through a material.

It is a still further object of the invention to provide a device for safely determining the permeation of chemicals which are highly toxic through a material.

Another object of the invention is to provide a device which in comparison to existing devices, requires a smaller volume of chemical, and optionally a smaller piece of material, for determining permeation of the chemical through the material.

Yet another object of the invention is to provide a simpler device for determining permeation of a chemical through a material, and one that may be constructed at substantially lower costs than prior art devices.

These and further objects of the invention will appear as the specification progresses.

BRIEF DESCRIPTION OF THE DRAWINGS

The invention will be described with reference to the accompanying drawings, illustrating a preferred embodiment of the invention. However, it should be understood that those skilled in the art may make changes in that embodiment without departing from the scope of the invention. The invention is therefore not limited to the embodiment shown and described herein, but is defined in the claims following this specification.

In the drawings.

DESCRIPTION OF THE PREFERRED EMBODIMENT

Figure 1:
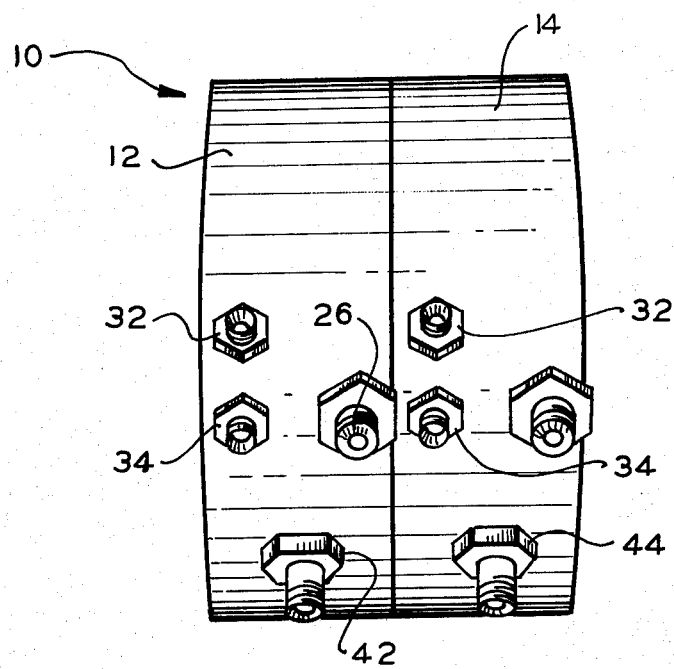
FIG. 1 is a perspective view showing a pair of permeation units forming a permeation cell in accordance with the present invention.

A device for testing various materials for permeation to various chemicals is about to be described with reference to the drawing. Although specific materials, chemicals, and structural features will be referred to, it is to be understood that these are exemplary only. Also, for purposes of coparison with an ASTM Reference Cell, selected materials and chemicals were used, but again these are exemplary only.

The device basically relies on the use of a permiation cell 10 which is shown in various details in FIGS. 1 to 4 to which reference will now be made.

Figure 2:
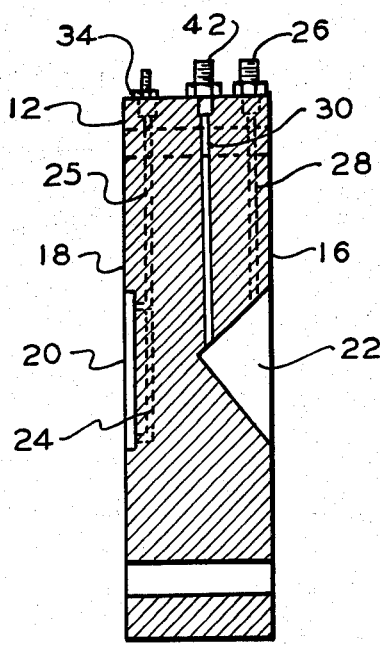
FIG. 2 is an elevational sectional view of a single permeation unit forming part of a cell, the view being taken along the line 2—2 of FIG. 4.

The cell 10 comprises two permeation units 12 and 14, of which one, denoted 12, is shown in FIG. 2. Each of these units is constructed of a chemically inert, machinable material such as a block of highly dense plastic, a fluoroplastic such as Teflon ®, glass, or stainless steel. Each unit is machined or otherwise formed on opposite faces 16, 18, to form a smooth, tight fit with another unit.

Each permeation unit has a shallow cylindrical well 20 in one face, and a conical well 22, in the opposite face. The purpose of these wells will be explained below. However, the face 18 having the cylindrical well will be referred to hereinafter as the "challenge side", and the other face 16 having the conical well 22 as the "collection side", for reasons which will also become apparent.

Figure 6A:
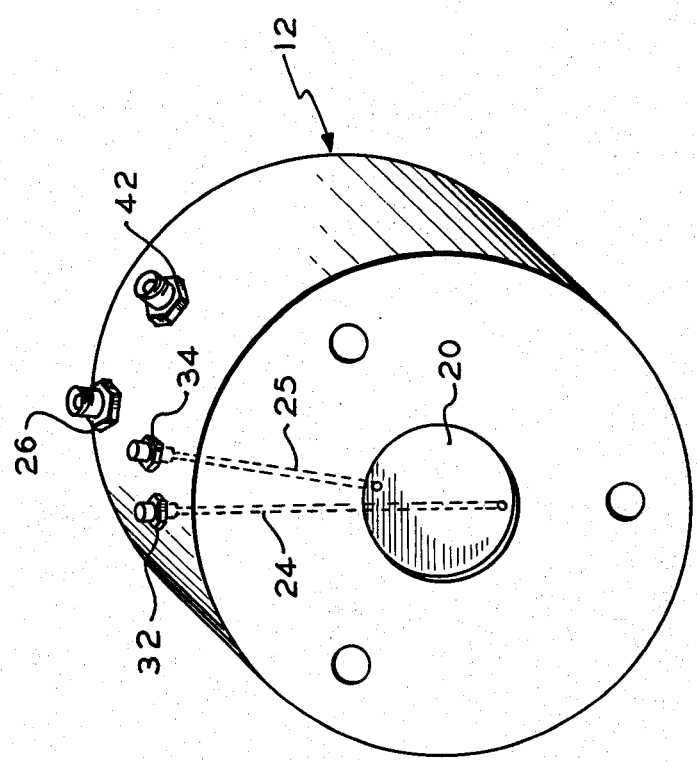
FIGS. 6A and 6B are, respectively, perspective views of permeation units, the first taken from the "collection side", and the other taken from the "challenge side" of a permeation cell.
Figure 6B:
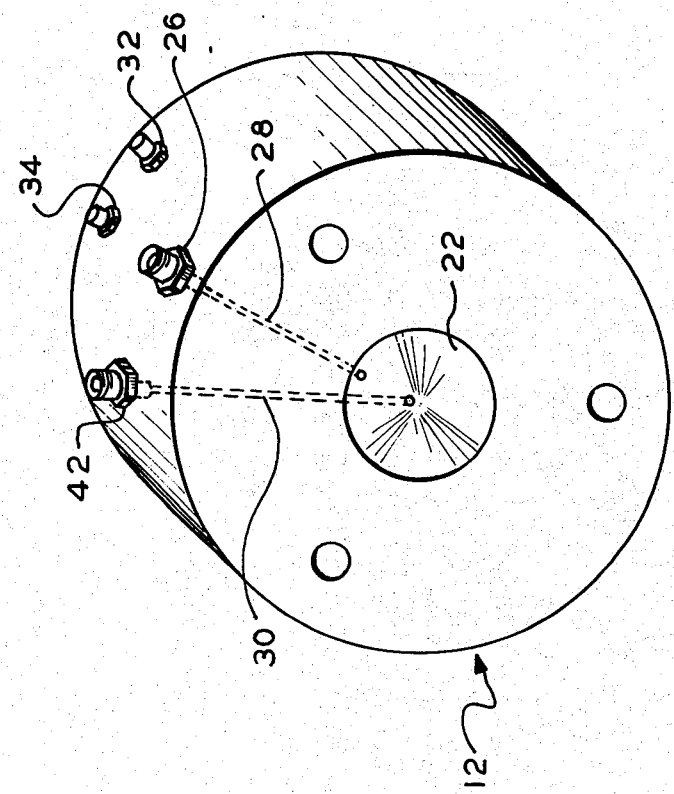

A bore 24 (FIGS. 2, 4 and 6B), connects the lower part of the cylindrical well to the outside of the unit where an entry port 32 (FIG. 1) is provided (e.g. a tube or compression fitting) for introducing a test chemical. A second bore, 25, connects the upper part of well 20 to port 34, and serves as a vent for the exit of air during the introduction of chemical.

The ports may be secured by any known means in order to effect a tight seal. The cell depicted in the drawings utilizes threaded holes to fasten the compression fittings to the unit body.

Two bores 28 and 30 (FIGS. 2 and 6A) connect the conical well 22 to the outside, where ports 26 and 42 (FIG. 1) are provided. Ports 26 and 42 again may be a tube or a compression fitting type, so that hoses, or tubings may be connected thereto for supplying and removing a collecting medium. One of these ports, 42, will be referred to as an inlet port, through which the collecting medium enters the unit, is carried down through bore 30, and exits through bore 28 and exit port 26.

Figure 3:
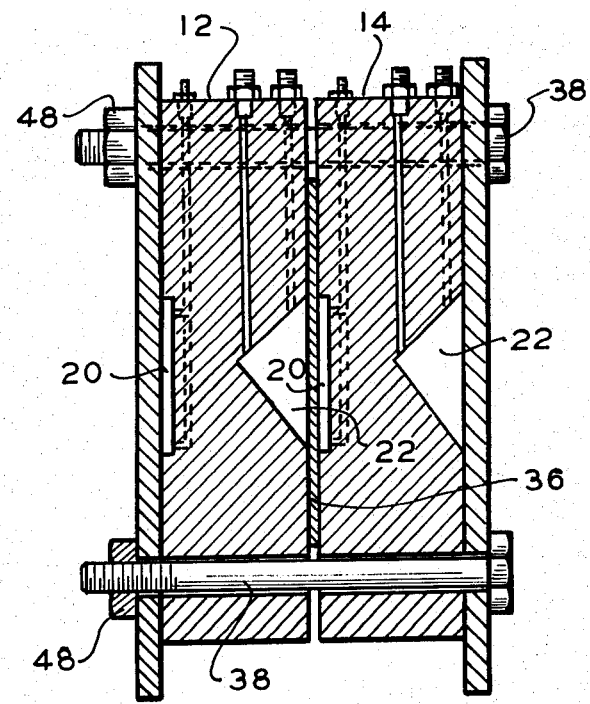
FIG. 3 is an elevational sectional view of a permeation cell in accordance with the invention.
Figure 4:
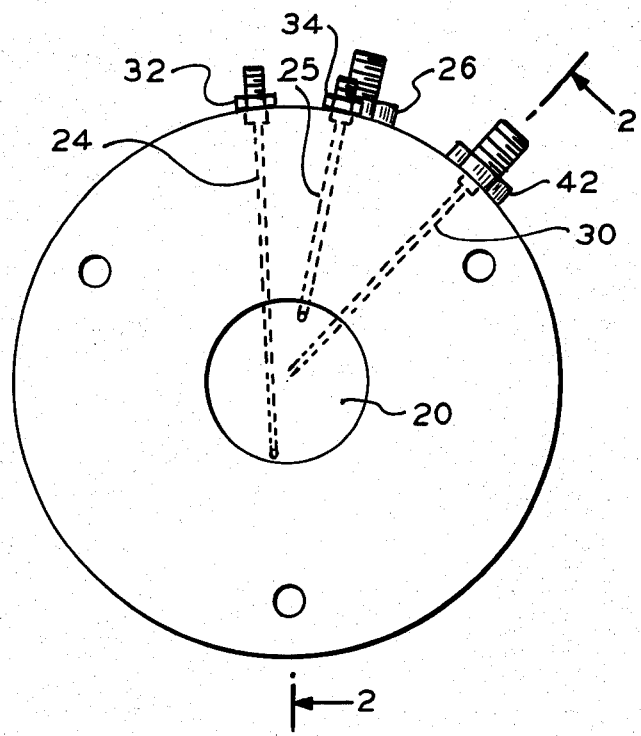
FIG. 4 is an end elevational view of the cell of FIG. 1, taken from the left side thereof.

A piece of test material 36, to be tested is placed between two units 12 and 14, as shown in FIG. 3, with the face of one unit 12 having the cylindrical well 20 facing the other unit face with the conical well 22. The two units are then securely fastened together between end plates 45 and 47, with the piece of material therebetween, as shown in FIG. 3, by bolts 38 and tightened by nuts 48 to seal the permeation unit.

The test chemical is then introduced into well 20, and the collecting medium passed into well 22. The collecting medium from port 26 can thereupon be subjected to an appropriate analytical technique, including those known in the prior art, to measure detectable concentrations of the test chemical that permeate through the test material.

Figure 7:
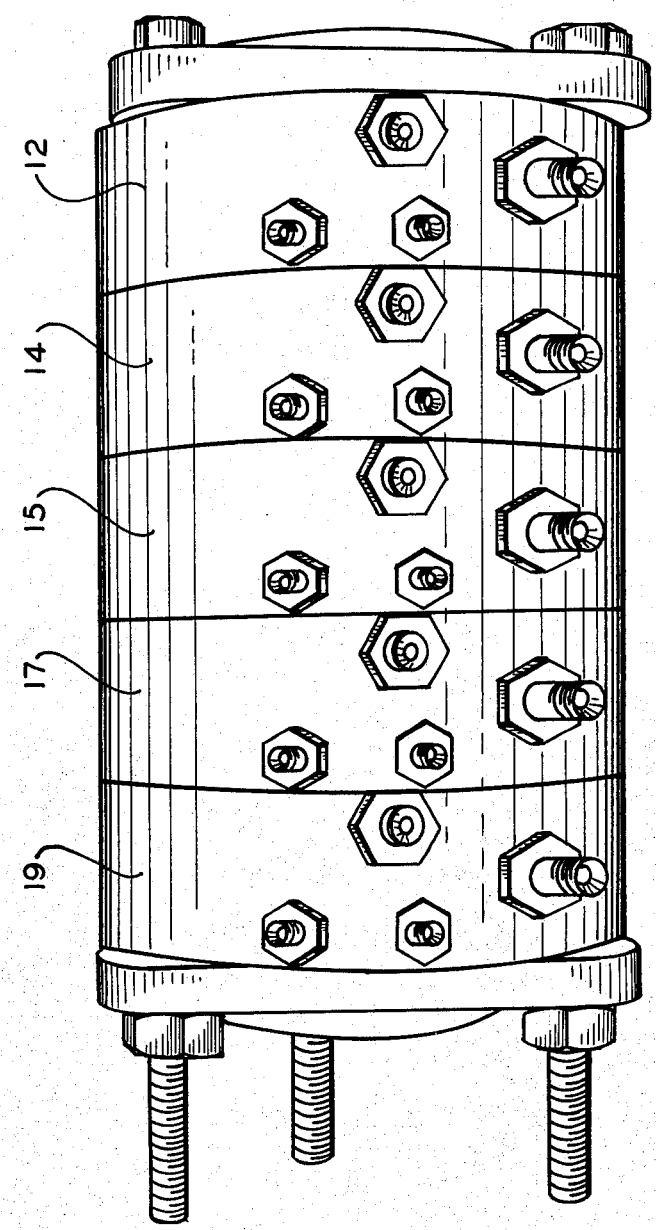
FIG. 7 is a generally elevational view, partly in perspective, depicting a multiple cell assembly.

Several units, 12, 14, 15, 17, and 19, as shown in FIGS. 1–5, may be secured together as shown in FIG. 7. The face of one cell with the cylindrical well is positioned opposite the face of another cell with a conical well. The entire stack is then securely fastened, with pieces of material to be tested between successive cells. In this case, the number of cells is always n-1 where n is an integer representing the number of units. Such an arrangement permits the simultaneous testing of several samples.

Using a permeation testing apparatus, a comparison of performance between the ASTM Reference Cell and the new cell of the invention was conducted. The material tested was Neoprene Rubber (18 mil thickness) and the challenge chemical was acetone. Table I represents the data generated in such study, and indicates that both cells are functionally equivalent.

TABLE I

| Pair of Tests | Permeation Rate (mg/m²/sec) | | Breakthrough Time (minutes) | |
|---|---|---|---|---|
| | ASTM Cell | Described Cell | ASTM Cell | Described Cell |
| 1 | 36.88 | 36.04 | 20 | 20 |
| 2 | 38.54 | 36.53 | 20 | 20 |
| 3 | 36.03 | 37.90 | 20 | 20 |
| 4 | 36.73 | 29.14 | 20 | 20 |
| 5 | 40.32 | 37.09 | 20 | 20 |
| 6 | 38.61 | 37.55 | 20 | 20 |

TABLE I-continued

| Pair of Tests | Permeation Rate (mg/m²/sec) | | Breakthrough Time (minutes) | |
|---|---|---|---|---|
| | ASTM Cell | Described Cell | ASTM Cell | Described Cell |
| 7 | 38.40 | 38.31 | 20 | 20 |
| 8 | 35.72 | 38.73 | 20 | 20 |
| 9 | 32.57 | 37.31 | 20 | 20 |
| Average: | 37.09 | 36.51 | 20 | 20 |

The permeation cell of the present invention permits the evaluation of test chemicals using as little as one milliliter (mL) volume. This cell has the following advantages in comparison to the ASTM Reference cell:
(1) 1-2 mL capacity (about 60 mL for ASTM Reference Cell), thus reducing the cost of analysis and the possibility of operator exposure;
(2) physically compact;
(3) increased sensitivity (i.e., more accurate detection of breakthrough);
(4) easier to handle than the ASTM Reference Cell;
(5) unbreakable; and
(6) less expensive (approximately one-third of the cost) of the ASTM cell.

The new cell, as determined in Table I, has been found equivalent in basic performance to the ASTM Reference Cell.

While the present invention has been particularly set forth in terms of specific embodiments thereof, it will be understood in view of the instant disclosure, that numerous variations upon the invention are now enabled to those skilled in the art, which variations yet reside within the scope of the present teaching.

Thus, for example, while the permeation units such as 12 and 14 in FIGS. 1-4 are shown in the form of generally cylindrical bodies, such units can be externally formed, if desired, as rectangular blocks, i.e. as rectangular parallelepipeds.

Figure 5:
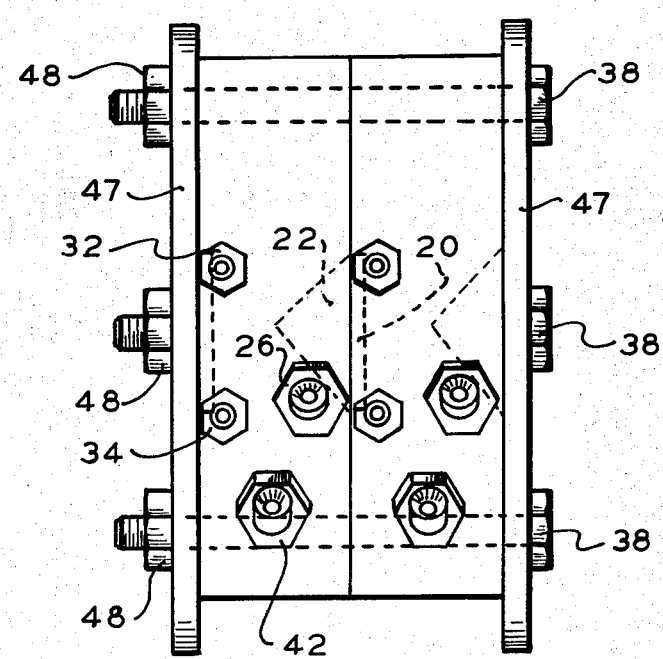
FIG. 5 is a top plan view of the cell of FIG. 3.

Further, while the permeation units such as in FIG. 2, are preferably formed into a permeation cell in the manner shown in FIGS. 3 and 5, it is also possible to utilize the units for testing permeation of a gas (e.g. a fluorinated hydrocarbon), by positioning the faces of the adjacent units so that the conical wells of each are opposed, with the material to be tested intervening. In such case the gas to be tested is bled through one conical well, with the opposed well being swept with the collecting medium (e.g. nitrogen). The collecting medium can then be analyzed downstream to determine concentration of the gas which is being tested for permeation.

Accordingly, the invention is to be broadly construed and limited only by the scope and spirit of the claims now appended hereto.

We claim:
1. A device for determining the permeation of test chemicals through a material, said device requires relatively small amount of the test chemicals, and comprising:
first and second blocks of chemically inert machinable material machined on opposite faces;
each of said blocks having a cylindrical well in one of said faces and a conical well in the other of said faces;
means to securely fasten said blocks together with a piece of the material to be tested between the face of one block having the cylindrical well and the face of the other block having the conical well;
means to introduce a test chemical into the block having the face with the cylindrical well facing the material to be tested, so that said test chemical enters said cylindrical well;
means to introduce a collecting medium into the other block having the face with the conical well facing the material to be tested, so that said medium enters said conical well; and
means to remove the collecting medium from the block having the face with the conical well facing the material to be tested, for providing said collecting medium with collected test chemical for analysis.

2. A device as claimed in claim 1, including means venting said cylindrical well, to facilitate flow of said test chemical to and from said well.

3. A device as claimed in claim 1 or 2 in which the blocks are clamped together by bolt means.

4. A device as claimed in claims 1 or 2 in which each said block is constructed of plastic.

5. A device as claimed in claims 1 or 2 in which each said block is constructed of a fluoroplastic.

6. A device as claimed in claims 1 or 2 in which each said block is constructed of glass.

7. A device as claimed in claims 1 or 2 in which each said block is constructed of stainless steel.

8. A cell for determining the permeation of a test chemical through a test material, said cell requires relatively small amount of the test chemical, and comprising:
first and second blocks of relatively chemically inert material, each of said blocks having a cylindrical well in one face thereof and a conical well in the opposed face thereof;
means to securely fasten said blocks together with a piece of the material to be tested between the face of one block having the cylindrical well and the face of the other block having the conical well;
means to flow a collecting medium to the conical well of the block having said conical well facing the material being tested, when a chemical to be tested for permeation is introduced into the cylindrical well of the other block; and
means to flow the collecting medium from the said conical well, to enable a measurement of the concentration of the chemical permeating the material being tested, in the collecting medium downstream of said conical well.

9. A cell as claimed in claim 8 in which the blocks are secured together with the material therebetween by bolt and end plate means.

10. A cell as claimed in claim 8 in which each block is constructed of plastic.

11. A cell as claimed in claim 10 in which each block is constructed of a fluoroplastic.

12. A cell as claimed in claim 8 in which each block is constructed of glass.

13. A cell as claimed in claim 8, including means for venting said cylindrical well, to facilitate introduction and withdrawal of said test chemical into said well.

14. A cell as claimed in claim 8 in which each block is constructed of stainless steel.

15. A multi-unit apparatus for determining the permeation of test chemicals through materials, said apparatus requires relatively small amount of the test chemicals and, comprising:

a plurality of blocks of relatively chemically inert material, each of said blocks having a cylindrical well formed in one of its faces and a conical well formed in the other of its faces;

means to securely fasten said blocks together with pieces of materials to be tested between the face of a block having the cylindrical well and the opposed face of another block having the conical well;

means to introduce and remove a chemical to be tested into each cylindrical well facing a piece of test material;

means to pass a collecting medium through each said conical well opposed to a said piece of test material; and means for withdrawing said collecting medium from said conical wells to enable testing of same to determine the concentration of the chemical permeating the material being tested, in the collecting medium fluid downstream of said conical wells.

16. Apparatus in accordance with claim 15, wherein n of said blocks are provided to enable testing of n-1 pieces of test material.

17. A permeation test cell for determining the permeation of a test chemical through a test material; said cell requires relatively small amount of the test chemical, and comprising:

first and second blocks of relatively chemically inert material, each said block having a cylindrical well in one face thereof, and a conical well in the opposed face thereof;

first and second flow channels passing from the periphery of each said block to its said cylindrical well to enable fluid flow to and from said well from the exterior of said block;

third and fourth channels passing from the periphery of each said block to its said conical well, to enable fluid flow to and from said well from the exterior of said block; and means for fastening said blocks in face-to-face sealing contact, with a piece of the material to be tested between the adjoining faces of the blocks;

said blocks being fastenable in a first configuration wherein the cylindrical well of one block is opposed to the conical well of the other, and in a second configuration wherein the conical well of one said block is opposed to the conical well of the second said block;

whereby in said first configuration, said material may be tested for permeation of a liquid, gaseous or solid said test chemical from said cylindrical well through said material and into said conical well, by introducing said test chemical into said cylindrical well, sweeping said conical well with a collecting medium downstream of said conical well, and whereby in said second configuration said material may be tested for permeation of a gaseous test chemical from one said conical well to the opposed conical well, by introducing said gaseous test chemical into one said conical well, sweeping said opposed conical well with a collecting medium, and analyzing said collecting medium downstream of said conical well.

18. A permeation test cell in accordance with claim 17, wherein one of said first or second flow channels comprises a vent, to facilitate introduction of a test chemical into said cylindrical well.

19. A test cell in accordance with claim 17, wherein the portions of said faces of each said block which adjoin the wells are planar to facilitate sealing contact between the fastened blocks.

* * * * *